United States Patent [19]

Schonberg

[11] Patent Number: 4,625,728

[45] Date of Patent: Dec. 2, 1986

[54] IMPROVING POULTRY EGG PRODUCTION

[76] Inventor: Michael Schonberg, 701 W. 177th St., New York, N.Y. 10033

[21] Appl. No.: 577,431

[22] Filed: Feb. 6, 1984

Related U.S. Application Data

[63] Continuation-in-part of Ser. No. 406,604, Aug. 9, 1982.

[51] Int. Cl.$^4$ .............................................. A61N 00/00
[52] U.S. Cl. ........................................ 128/395; 119/1
[58] Field of Search ..................... 128/23, 24.1, 303.1, 128/362, 395–398, 633, 634; 604/20; 119/1, 21; 252/301.4 R; 313/486; 362/1, 2, 32, 84, 260

[56] References Cited

U.S. PATENT DOCUMENTS

| | | | |
|---|---|---|---|
| 1,922,157 | 8/1933 | Fox | 119/31 |
| 2,270,096 | 1/1942 | Warp | 88/109 |
| 3,825,792 | 7/1974 | Rokosz et al. | 313/487 |

OTHER PUBLICATIONS

"Physiological Development of Cockerels as Influenced by Selected Wavelengths of Environmental Light", Foss et al., Poultry Sci., 1972.
"Sexual Maturity and Subsequent Reproductive Performance of White Leghorn Chickens Subjected to Different Parts of the Light Spectrum", Harrison et al., Sci., 1969.
"Effect of Wave Length of Light on Growth and Reproduction in Japanese Quail", Woodward et al., Sci., 1969.
"Controlled Photoperiodic Environments for Food Animals", Tucker et al., Sci., 1982.

Primary Examiner—Edward M. Coven
Assistant Examiner—Max F. Hindenburg
Attorney, Agent, or Firm—Nolte, Nolte and Hunter

[57] ABSTRACT

A method of improving egg production in poultry by irradiating poultry with energy levels, the first one of which is within a wavelength band of 600 to 670 nanometers and is delivered at a rate of at least $10^{13}$ quanta/second/cm$^2$, and, in the case where this first radiation is less than $10^{13}$ quanta/second/cm$^2$, at least 75% of the total delivered energy is within the first wavelength band. The second radiation energy level is within a wavelength band of 400 to 600 nanometers and is delivered at a rate of at least $10^{14}$ quanta/second/cm$^2$, and, in the case where this second radiation is less than $10^{14}$ quanta/second/cm$^2$, at least 80% of the total delivered energy is within the wavelength band of 400–600 nanometers. The invention also includes a control of the time during which the irradiation is delivered.

8 Claims, No Drawings

IMPROVING POULTRY EGG PRODUCTION

BACKGROUND OF THE INVENTION

This application is a continuation-in-part application of U.S. application Ser. No. 406,604, filed Aug. 9, 1982.

The environmental aspects of raising animals, and specifically poultry, are known to have a direct relationship to the time at which the animals mature. In poultry, this corresponds to the time at which the chickens are available for market and when egg production commences, as well as the quality and quantity of such egg production. In regard to poultry raising, it has been proposed to utilize red filters over the illumination sources or red windows in the hen house in an effort to decrease cannibalism among the poultry. Poultry have a strange attraction to the sight of blood, particularly blood appearing on other members of the flock. When a chicken has blood on it, the other chickens peck at that chicken and ultimately this pecking spreads in rather epidemic proportions throughout the flock. Use of red light, either through filtering natural sunlight or filtering incandescent illumination, will make the red blood appear somewhat black and, thus, will inhibit pecking among members of the flock and will prevent cannibalism. Additionally, the use of infrared radiation as a source of heat, particularly in an incubator or brooder, for incubating the eggs and for brooding the chicks is also a known practice.

U.S. Pat. No. 4,336,809, to Clark discloses that when a dye containing hematoporphyrin or hematoporphyrin derivatives, which have been administered intraveneously, is irradiated with a high intensity red light having an absorption peak at a wavelength of about 631 nanometers, a cytotoxic effect is achieved against malignant tissue. The light source for the Clark disclosure is a high energy xenon ion laser arranged for simultaneous lasing at wavelengths from about 406 to 427 nanometers and at a wavelength of about 626 nanometers.

U.S. Pat. No. 3,986,513 to Stuhl discloses apparatus for irradiating the skin for therapeutic and healing purposes and especially for treatment of psoriasis. The Stuhl disclosure, however, is directed to topical treatment of a local dermal condition, and is not related to animal conditioning treatment.

Thus, it is known that there are some beneficial effects that may be obtained from using radiation, including infrared radiation, generally termed red light, on poultry and in human treatment.

Nevertheless, faced with the information regarding poultry, the vast majority of poultry raisers use clear incandescent or white fluorescent artificial illumination sources. One drawback in placing red filters over the artificial illumination sources is that this represents an energy loss, since there are light transmission losses in the filter. Also, the kind of filters used are generally of poor filtering quality and are not totally effective in passing only red light. Similarly, infrared incandescent lighting generally produces too much heat. A large amount of heat in poultry is known to produce stressful conditions in the organisms, and this is then counterproductive when attempting to increase the production of the flock.

The use of special lamps in raising plants has also become quite popular these days. These "grow lamps" are usually intended as a source of artificial sunlight with the added convenience that exact photoperiods can be obtained by control of such lamps. See U.S. Pat. No. 4,146,993 and U.S. Pat. No. 3,931,695.

SUMMARY OF THE INVENTION

By the present invention there is provided a means for effecting physiological response by irradiation with certain energy levels for controlled periods of time so that various methods of treatment can be devised to produce desired effects in animal husbandry.

One of the energy levels of the invention includes radiation within a wavelength band of from 600-670 nanometers, which is a "near red" band width. This energy can be effective when the rate delivered to the subject of the treatment is at least $10^{13}$ quanta/second/cm$^2$, and, if the rate of delivery of this first energy level radiation is below $10^{13}$ quanta/second/cm$^2$, at least 75% of the total energy delivered is within the 600-670 namometer wavelength band. It has been found that a fluorescent light source is particularly useful for providing the effective radiation, especially a fluorescent light having a phosphor of fluoromagnesium germanate with a peak fluorescence of about 650 nanometers.

A second energy level according to the present invention is radiation within a wavelength band of 400-600 nanometers, which near the green band. This radiation can be effective at a rate of delivery of at least $10^{14}$ quanta/second/cm$^2$, and, if the rate of delivery is below $10^{14}$ quanta/second/cm$^2$, at least 80% of the total delivered energy is within a wavelength band of 400-600 nanometers. It has been found that fluorescent light source is particularly useful for providing this effective radiation, especially a fluorescent light having a phosphor of cerium terbium magnesium aluminate with a fluorescence peaking at a wavelength of about 544 nanometers.

The inventive use of the near red fluorescent lamp on poultry has been found to modify body weight, promote sexual development, improve efficiency of food consumption, reduce mortality caused by stress and cannibalism, and increase egg productivity.

Exclusive exposure of new-born animals to this near red illumination will accelerate their sexual development. Precocious sexual maturation can be of economic advantage in animal husbandry and poultry management.

Animals grown under this near red light are more frugal in their eating habits, thereby providing an economic benefit by decreased feed costs. Moreover, use of this light does not reduce meat and egg quality, in fact, they are actually improved.

By housing animals so that this near red light is the exclusive illumination, the animals are calmed down and exhibit less stress, with the important consequences of lower morbidity and mortality. The influence of this light will ameliorate stressful situations, thereby providing a great economic benefit in animal husbandry, fish, and poultry management.

Birds exposed to this near red light will produce more eggs than if exposed to natural light or fluorescent or incandescent illumination.

With respect to poultry raising, the present invention teaches a method, wherein a lamp producing near red radiation is used for periods of illumination each day that are shorter than normal ambient light periods. Once the chickens reach a proper body weight for sexual maturation, as set forth in standard reference books on animal husbandry, the illumination periods are drastically increased to periods that are longer than normal ambient light periods; this induces maximal sexual development. The invention teaches another method, wherein a lamp having an illumination spectrum in the green band is used to accelerate growth until optimum weight for sexual maturation is reached, and then the "near red" radiation lamp is employed.

Furthermore, in this regard, the present invention includes another method wherein a light source having an illumination spectrum in the green band is used in management of embryo growth by irradiation for a controlled period of time, until an optimum embryo weight is attained, either at or before term. Alternatively, a light source providing near red radiation is employed for a controlled period of time, in order to accelerate the embryo's maturation which, in the case of poultry, results in earlier hatching. Both methods will reduce the time needed for either embryonal growth or embryonic maturation, thus resulting in considerable savings in time and money. The two sources of light can be used individually, in sequence, or in various combinations.

The lamp of the fluorescent kind can be formed as long tubes with internal electrodes with the appropriate electrical connections at either end. The construction of the lamp, save for the spectral emission and manner in which it is obtained, form no part of this invention. These kinds of lamps are advantageous in that they do not involve filters or exterior coatings and the specific wavelengths of the output are a function totally attributed to the internal "phosphor." The "phosphor" in the lamp producing the "near red" band illumination is comprised of magnesium fluorogermanate. In this lamp, the fluorescence peaks at a wavelength of approximately 658 nanometers. The fluorescent lamp that is used to produce the green band radiation uses as its "phosphor" cerium terbium magnesium aluminate that has a peak emission at a wavelength of approximately 544 nanometers.

The present invention recognizes that the use of red light is beneficial, however, it has been determined that the selection of the actual wavelengths is much more critical than simply using "red light," and also that there are specific light sources, particularly fluorescent tubes, which can be constructed to provide these desired wavelengths of radiation. Therefore, it is an object of the present invention to provide a method for increasing the production of poultry by use of specialized visible radiation.

It is another object of the present invention to provide a method using a fluorescent lamp for providing the specialized radiation for the animals.

It is another object of the present invention to provide a method for increasing poultry production by using specialized wavelengths of radiation for specific periods of time and at specific times during the life of the animal.

For a better understanding of the present invention, together with other and further objects, reference is made to the following description, and its scope will be pointed out in the appended claims.

DETAILED DESCRIPTION OF THE INVENTION

The present invention is a method of effecting physiological responses by irradiating with discovered advantageous levels of energy. In particular, a first advantageous method involves irradiating poultry with near-red radiation, wherein the preponderance of the emission has wavelengths lying between 600 and 670 nanometers, and preferably between 620 and 670 nanometers. When the rate of delivery of this radiation is at least $10^{13}$ quanta/second/cm$^2$, an amount of other radiation can be present. However, when the rate of delivery falls below $10^{13}$ quanta/second/cm$^2$, at least 75% of the total radiation must be within the 600-670 wavelength band. Generally, it is desirable to have 75% or more of the radiation energy produced by the source, such as a lamp, falling within these wavelength limits. Experience has indicated that far red radiation has been shown to be inhibitory to sexual development.

The radiation source is preferably a phosphor of magnesium fluorogermanate whose fluorescence peaks at wavelengths of 650 nanometers, thereby falling exactly within the near-red range taught by the present invention. The following chart indicates the spectral distribution of the total emission from this lamp.

| Wavelength Band (Nanometers) | % Total Emission |
| --- | --- |
| <600 | 9 |
| 600-620 | 2 |
| 620-640 | 16 |
| 640-660 | 33 |
| 660-680 | 35 |
| 680-700 | 4 |
| >700 | 1 |

In one method of the present invention, poultry are illuminated by this inventive lamp for a normal period, wherein the inventive light source provides a tranquilizing influence. This has been found to be specifically effective on layer pullets. Nevertheless, undesirable premature sexual development is prevented by using shortened photoperiods of illumination, for example, only 8 to 9 hours total illumination per day. Thus, the near red light provides a nonstressful environment but, by controlling the length of time of its use, is prevented from causing premature sexual development before proper body weight is achieved. One the proper body weight has been achieved, the photoperiods are drastically lengthened up to 14 to 16 hours of illumination per day, for example. This will then induce maximal sexual development, gonads will grow dramatically, and egg production will be improved significantly. As is well known, the proper body weight indicating sexual maturation is different for almost every breed or strain of chicken. There are growth charts readily available that indicate the proper weight for housing of layer hens, i.e., when egg production should commence. Nevertheless, the hatchery, when supplying the pullets, will provide a recommended weight for commencing egg production.

The present invention also teaches another method involving radiation falling within a narrow green band of wavelengths between 400 and 600 nanometers. When the rate of delivery of this second level of radiation is $10^{14}$ quanta/second/cm$^2$, other radiation energy can be present. However, when the rate of delivery falls below $10^{14}$ quanta/second/cm$^2$, at least 80% of the total radiation must be within the 400-600 wavelength band. Generally, it is preferable that the radiation be derived from a fluorescent light that has 80% of its emitted radiation falling within this narrow green band.

It has been indicated by experimentation in the poultry industry that radiation at wavelengths in this band has the valuable characteristic of increasing the growth rate of very young birds, including embryonic growth. Additionally, lobsters have also evidenced increased growth rate when subjected to illumination at these wavelengths. This lamp includes as its phosphor cerium terbium magnesium aluminate, and the peak percentage of total emissions of this lamp lie at wavelengths of approximately 544 nanometers. The following chart indicates the spectral distribution of the total emission from this lamp.

| Wavelength Band (Nanometers) | % Total Emission |
|---|---|
| <480 | 9.7 |
| 480–500 | 11.4 |
| 500–520 | 1.2 |
| 520–540 | 3.6 |
| 540–560 | 50.7 |
| 560–580 | 2.4 |
| 580–600 | 9.2 |
| 600–620 | 2.0 |
| >620 | 9.8 |

It has been found that radiation within this specific wavelength band promotes growth in poultry. Thus, the present invention teaches a method for improving poultry production by first using the above fluorescent illumination in the green band to illuminate layaer pullets until "mature body weight," which is the proper body weight for sexual development to proceed has been obtained. As set forth hereinabove, this weight is easily learned and is usually provided by the hatchery. It has been found that such proper body weight for sexual development is arrived at 2 to 4 weeks earlier than when using conventional illumination sources. At the time when the mature body weight is achieved, the illumination sources are switched and in place of the green band illumination the poultry are illuminated with the near red radiation described above. Through tests and experiments in the poultry industry, the inventor has found that near red radiation produces maximal sexual development. Thus, use of these two radiation sources results in a significant economic benefit, due to earlier and more prolonged oviposition with no detriment to egg quality. Also, embryo maturation will be accelerated when the animals are exposed to near red radiation.

The present invention also contemplates a radiation delivery system employing fibre optics or other solid optical delivery system. In this system, the fibre optic distribution of the specific wavelength radiation would be such that each animal or each animal container would obtain illumination via the solid optical delivery system but the illumination would originate from a single source or location. The light source being either or both of the above-described inventive light sources. In this way, the homogeneity of photon distribution will be improved; there will be no temperature increases caused by the heat radiation of the illumination sources; the system will be more efficient, since fewer bulbs will be required and, thus, will become more energy efficient and improve the economy of the operation; the maintenance of the light fixtures will be drastically improved, since less cleaning and changing of bulbs and the like will be required because the light sources can be somewhat removed from the actual location of the animals; and, finally, safety will be improved, since there will be fewer electrical outlets and less wiring involved.

As an added feature of the present invention, it has been found that the lamp providing illumination in the near red area of the optical spectrum is of further utility, since it produces radiation that is essentially invisible to insects. A typical problem involved with animal illumination systems is that the light fixtures attract large quantities of insects, however, because the present invention teaches a lamp producing radiation that is invisible to insects, no such insect attraction is present. This means that in areas where insects can be a nuisance, both the health hazard of the insect and the burden of increased lamp maintenance due to the insect infestation can be almost completely avoided.

Finally, it has also been discovered that control over sexual maturation in poultry can be controlled by use of the near red irradiation in order to advance maturation, and by use of the green wavelength band to retard maturation. This is believed to occur by control of steroid biosynthesis and, in particular, sexual maturation is controlled by estrogen, testosterone production and progesterone production. In poultry, generally when these steroids are increased, sexual maturation is increased.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed:

1. A method for improving egg production in poultry comprising:
    irradiating said poultry with a first radiation comprising a green radiation within a wavelength band of 400 to 600 nanometers until said poultry have attained proper body weight for sexual development to proceed; said green radiation being delivered to said poultry at a rate of at least $10^{14}$ quanta/second/cm$^2$ or, if said green radiation is delivered at a rate of less than $10^{14}$ quanta/second/cm$^2$, said green radiation comprising at least 80% of said first radiation; and
    subsequently irradiating said poultry with a second radiation comprising a near-red radiation within a wavelength band of 600 to 670 nanometers; said near-red radiation being delivered to said poultry at a rate of at least $10^{13}$ quanta/second/cm$^2$ or, if said near-red radiation is delivered at a rate of less than $10^{13}$ quanta/second/cm$^2$, said near-red radiation comprising at least 75% of said second radiation.

2. The method of claim 1, wherein said second radiation comprises at least a preponderance of said near-red radiation.

3. The method of claim 2, wherein the source of said second radiation is a first fluorescent light and at least 75% of said second radiation is said near-red radiation.

4. The method of claim 3, wherein said second radiation from said second fluorescent light has a spectral distribution with no more than about 1% of its radiation with a wavelength greater than about 700 nanometers.

5. The method of claim 4, wherein said near-red radiation is within a wavelength band of 620 to 670 nanometers.

6. The method of claim 5, wherein said second fluorescent light comprises a phosphor of magnesium fluorogermanate having a fluorescence peaking at a wavelength of about 650 nanometers.

7. The method of claim 1, wherein the source of said first radiation is a first fluorescent light and at least 80% of said first radiation is said green radiation.

8. The method of claim 7, wherein said first fluorescent light comprises a phosphor of cerium terbium magnesium aluminate having a fluorescence peaking at a wavelength of about 544 nanometers.

* * * * *

UNITED STATES PATENT AND TRADEMARK OFFICE
CERTIFICATE OF CORRECTION

PATENT NO. : 4,625,728
DATED : December 2, 1986
INVENTOR(S) : Michael Schonberg

It is certified that error appears in the above-identified patent and that said Letters Patent are hereby corrected as shown below:

Column 5, line 56 "first" should be -- second --.

Signed and Sealed this

Twenty-fourth Day of March, 1987

*Attest:*

DONALD J. QUIGG

*Attesting Officer*  *Commissioner of Patents and Trademarks*